United States Patent [19]

Dubs et al.

[11] Patent Number: 5,175,312

[45] Date of Patent: Dec. 29, 1992

[54] 3-PHENYLBENZOFURAN-2-ONES

[75] Inventors: Paul Dubs, Marly; Rita Pitteloud, Praroman, both of Switzerland

[73] Assignee: Ciba-Geigy Corporation, Ardsley, N.Y.

[21] Appl. No.: 754,180

[22] Filed: Aug. 27, 1991

Related U.S. Application Data

[63] Continuation of Ser. No. 572,748, Aug. 23, 1990, abandoned.

[30] Foreign Application Priority Data

Aug. 31, 1989 [CH] Switzerland ............... 3153/89-9

[51] Int. Cl.⁵ .......................................... C07D 307/79
[52] U.S. Cl. .................................... 549/307; 549/310
[58] Field of Search ............................. 549/307, 310

[56] References Cited

U.S. PATENT DOCUMENTS

| | | | |
|---|---|---|---|
| 4,325,863 | 4/1982 | Hinsken et al. | 524/722 |
| 4,338,244 | 7/1982 | Hinsken et al. | 529/97 |
| 4,366,240 | 12/1982 | Lässig et al. | 430/542 |
| 4,611,016 | 9/1986 | Hinsken et al. | 529/97 |

FOREIGN PATENT DOCUMENTS

| | | |
|---|---|---|
| 61-138648 | 6/1986 | Japan. |
| 61-145239 | 7/1986 | Japan. |
| 2042562 | 9/1980 | United Kingdom. |

OTHER PUBLICATIONS

Derwent Abst. 86-207397/32.
Derwent Abst. 86-214695/33.
Research Disclosure 28888 (Apr. 1988).

Primary Examiner—Jane T. Fan
Attorney, Agent, or Firm—Luther A. R. Hall

[57] ABSTRACT

Novel compounds of the formula I

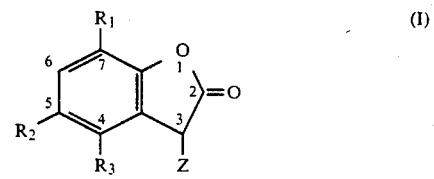

in which $R_1$ is $C_{13}$–$C_{30}$alkyl, $R_2$ is hydrogen, $C_1$–$C_{10}$alkyl, $C_5$–$C_{12}$cycloalkyl, $C_5$–$C_7$cycloalkyl which is substituted by $C_1$–$C_4$alkyl, or is phenyl or $C_7$–$C_{12}$phenylalkyl, $R_3$ is hydrogen or $C_1$–$C_4$alkyl and Z is phenyl, phenyl which is substituted by $C_1$–$C_8$alkyl, $C_1$–$C_4$alkoxy or chlorine, a group

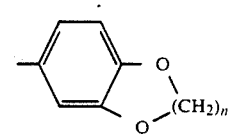

in which n is 1 or 2 or a group

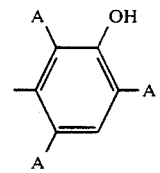

in which the radicals A independently of one another are $C_1$–$C_8$alkyl, methoxy or ethoxy, are suitable for stabilizing organic material against oxidative, thermal and actinic degradation.

8 Claims, No Drawings

3-PHENYLBENZOFURAN-2-ONES

This is a continuation of application Ser. No. 572,748, filed on Aug. 23, 1990, now abandoned.

The present invention relates to novel 3-phenylbenzofuran-2-ones, to the organic material stabilized by means of them against thermal, oxidative and actinic degradation and to the use of these compounds for stabilizing organic materials.

The use of some benzofuran-2-ones as stabilizers for organic polymers is known from GB-A 2,042,562 or BE-A 881,496 and also the Derwent Abstracts 86-207 397/32 and 86-214 695/33 and the Research Disclosure 28888 (1988). Some benzofuran-2-ones and their use in colour photography are described in US T 904,003.

The present invention relates to compounds of the formula I

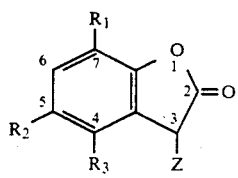

in which $R_1$ is $C_{13}-C_{30}$alkyl, $R_2$ is hydrogen, $C_1-C_{10}$alkyl, $C_5-C_{12}$cycloalkyl, $C_5-C_7$cycloalkyl which is substituted by $C_1-C_4$alkyl, or is phenyl or $C_7-C_{12}$phenylalkyl, $R_3$ is hydrogen or $C_1-C_4$alkyl and Z is phenyl, phenyl which is substituted by $C_1-C_8$alkyl, $C_1-C_4$alkoxy or chlorine, a group

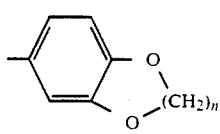

in which n is 1 or 2 or a group

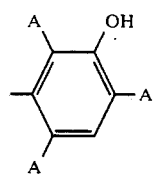

in which the radicals A independently of one another are $C_1-C_8$alkyl, methoxy or ethoxy.

Examples of $R_1$ as $C_{13}-C_{30}$alkyl, preferably $C_{13}-C_{20}$alkyl, are tridecyl, tetradecyl, pentadecyl, hexadecyl, heptadecyl, octadecyl, nonadecyl and icosyl. Preferably, alkyl radicals of this type which are branched in the 1-position are especially 1-($C_{12}-C_{16}$alkyl)ethyl, for example 1-dodecylethyl, 1-tridecylethyl, 1-tetradecylethyl, 1-pentadecylethyl and 1-hexadecylethyl. 1-Dodecylethyl and 1-hexadecylethyl are particularly preferred.

Examples of $R_2$ as $C_1-C_{10}$alkyl are methyl, ethyl, propyl, butyl, pentyl, hexyl, heptyl, octyl, nonyl and decyl. $R_2$ is preferably $C_1-C_4$alkyl, in particular methyl and tert-butyl.

Examples of $R_2$ as $C_5-C_{12}$cycloalkyl are cyclopentyl, cyclohexyl, cycloheptyl, cyclooctyl, cyclononyl, cyclodecyl, cycloundecyl or cyclododecyl. $R_2$ is also preferably $C_5-C_7$cycloalkyl, especially cyclohexyl.

Examples of $R_2$ as $C_5-C_7$cycloalkyl which is substituted by $C_1-C_4$alkyl are methylcyclohexyl and tert-butylcyclohexyl.

Examples of $R_2$ as $C_7-C_{12}$phenylalkyl are benzyl and 2-phenylethyl.

Examples of $R_3$ as $C_1-C_4$alkyl are methyl, ethyl, propyl and butyl. $R_3$ is preferably methyl.

Examples of Z as substituted phenyl are o-, m- or p-methylphenyl, o-, m- or p-ethylphenyl, o-, m- or p-butylphenyl, o-, m- or p-methoxyphenyl, o-, m- or p-ethoxyphenyl, o-, m- or p-chlorophenyl and 2,4,6-trimethyl-5-hydroxyphenyl.

Z is preferably phenyl.

Compounds of the formula I in which $R_1$ is $C_{13}-C_{20}$alkyl and Z is phenyl are preferred.

Compounds of the formula I in which $R_1$ is $C_{14}-C_{18}$alkyl are also preferred.

Compounds of the formula I in which $R_2$ is hydrogen, $C_1-C_4$alkyl, cyclohexyl, phenyl or benzyl are also preferred.

Compounds of the formula I in which $R_2$ is hydrogen or $C_1-C_4$alkyl are also preferred.

It is particularly preferable for $R_3$ to be hydrogen or methyl.

Compounds of the formula I in which $R_1$ is $C_{14}-C_{18}$alkyl and $R_2$ and $R_3$ independently of one another are hydrogen or $C_1-C_4$alkyl are of particular interest.

The following are preferred examples of compounds of the formula I:

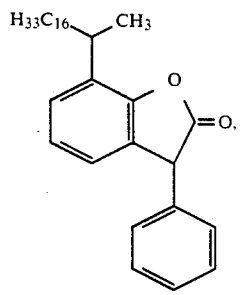
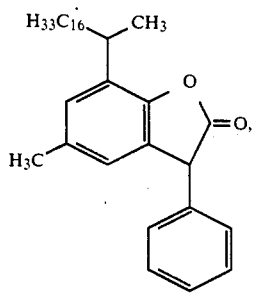
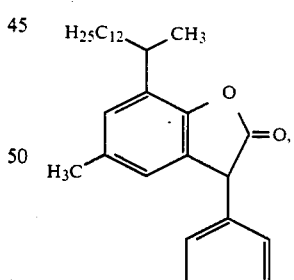
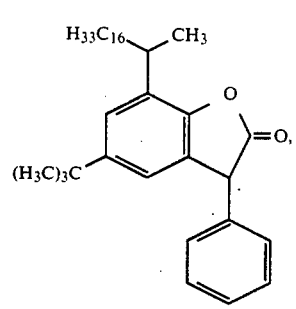
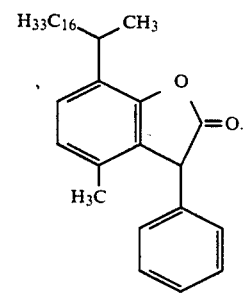

3-Phenyl-5-methyl-7-(1'-dodecylethyl)-benzofuran-2-one is a particularly preferred compound of the formula I.

The compounds of the formula I are suitable for stabilizing organic materials against thermal, oxidative or actinic degradation.

The following are examples of materials of this type:

1. Polymers of monoolefins and diolefins, for example polypropylene, polyisobutylene, polybutene-1, polymethylpentene-1, polyisoprene or polybutaadiene, as well as polymers of cycloolefins, for instance of cyclopentene or norbornene, polyethylene (which optionally can be crosslinked, for example high density polyethylene (HDPE), low density polyethylene (LDPE) and linear low density polyethylene (LLDPE).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and its mixtures with low density polyethylene (LDPE), propylene/but-1-ene, propylene/isobutylene, ethylene/but-1-ene, ethylene/hexene, ethylene/methylpentene, ethylene/heptene, ethylene/octene, propylene/butadiene, isobutylene/isoprene, ethylene/alkyl acrylate, ethylene/alkyl methacrylate, ethylene/vinyl acetate or ethylene/acrylic acid copolymers and their salts (ionomers) and terpolymers of ethylene with propylene and a diene, such as hexadiene, dicyclopentadiene or ethylidene-norbornene; as well as mixtures of such copolymers and their mixtures with polymers mentioned in 1) for example polypropylene/ethylene-propylene-copolymers, LDPE/ethylene-vinyl acetate-copolymers, LDPE/ethylene-acrylic acid-copolymers, LLDPE/ethylene-vinyl acetate-copolymers and LLDPE/ethylene-acrylic acid-copolymers.

3a. Statistical or alternating copolymers of $\alpha$-olefins with carbon monoxide.

3b. Hydrocarbon resins (for example $C_5$–$C_9$) and hydrogenated modifications thereof (for example tackifiers).

4. Polystyrene, poly-(p-methylstyrene), poly-($\alpha$-methylstyrene).

5. Copolymers of styrene or $\alpha$-methylstyrene with dienes or acrylic derivatives, for example styrene/butadiene, styrene/acrylonitrile, styrene/alkyl methacrylate, styrene/butadiene/alkyl acrylate, styrene/maleic anhydride, styrene/acrylonitrile/methyl acrylate; mixtures of high impact strength from styrene copolymers and another polymer, for example from a polyacrylate, a diene polymer or an ethylene/propylene/diene terpolymer; and block copolymers of styrene, for example styrene/butadiene/styrene, styrene/isoprene/styrene, styrene-ethylene/butylene-styrene or styrene-ethylene/propylene-styrene.

6. Graft copolymers of styrene or $\alpha$-methylstyrene, for example styrene on polybutadiene, styrene on polybutadiene-styrene or polybutadiene-acrylonitrile; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene, styrene and alkyl acrylates or methacrylates on polybutadiene, styrene and acrylonitrile on ethylene/propylene/diene terpolymers, styrene and acrylonitrile on polyalkylacrylates or polyalkylmethacrylates, styrene and acrylonitrile on acrylate/butadiene copolymers, as well as mixtures thereof with the copolymers listed under 5), for instance the copolymer mixtures known as ABS-, MBS-, ASA- or AES-polymers.

7. Halogen-containing polymers, such as polychloroprene, chlorinated rubbers, chlorinated or sulfochlorinated polyethylene, copolymers of ethylene and chlorinated ethylene, epichlorohydrin homo- and copolymers, in particular polymers from halogen-containing vinyl compounds, for example polyvinyl chloride, polyvinylidene chloride, polyvinyl fluoride, polyvinylidene fluoride, as well as copolymers thereof, for example vinyl chloride/vinylidene chloride, vinyl chloride/vinyl acetate or vinylidene chloride/vinyl acetate copolymers.

8. Polymers which are derived from $\alpha,\beta$-unsaturated acids and derivatives thereof, such as polyacrylates and polymethacrylates, polyacrylamides and polyacrylonitriles.

9. Copolymers from the monomers mentioned under 8) with each other or with other unsaturated monomers, for instance acrylonitrile/butadiene, acrylonitrile/alkyl acrylate, acrylonitrile/alkoxyalkyl acrylate or acrylonitrile/vinyl halogenide copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinyl butyral, polyallyl phthalate or polyallylmelamine; as well as their copolymers with olefins mentioned in 1) above.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and those polyoxymethylenes which contain comonomers for example ethylene oxide; polyacetals modified with thermoplastic polyurethanes, acrylates or MBS.

13. Polyphenylene oxides and sulfides, and mixtures thereof with polystyrenes or polyamides.

14. Polyurethanes which are derived from polyethers, polyesters or polybutadienes with terminal hydroxyl groups on the one side and aliphatic or aromatic polyisocyanates on the other side, as well as precursors thereof.

15. Polyamides and copolyamides which are derived from diamines and dicarboxylic acids and/or from aminocarboxylic acids or the corresponding lactams, such as polyamide 4, polyamide 6, polyamide 6/6, 6/10, 6/9, 6/12 and 4/6, polyamide 11, polyamide 12, aromatic polyamides obtained from m-xylene, diamine and adipic acid; polyamides prepared from hexamethylenediamine and isophthalic and/or terephthalic acid and optionally an elastomer as modifier, for example poly-2,4,4-trimethylhexamethylene terephthalamide or poly-m-phenylene isophthalamide. Block copolymers of the aforementioned polyamides with polyolefins, olefin copolymers, ionomers or chemically bonded or grafted elastomers; or with polyethers, for instance with polyethylene glycol, polypropylene glycol or polytetramethylene glycol. Further, polyamides or copolyamides modified with EPDM or ABS; and polyamides condensed during processing "RIM-polyamide systems".

16. Polyureas, polyimides, polyamide-imides and polybenzimidazoles.

17. Polyesters which are derived from dicarboxylic acids and diols and/or from hydroxycarboxylic acids or the corresponding lactones, such as polyethylene terephthalate, polybutylene terephthalate, poly-1,4-dimethylolcyclohexane terephthalate and polyhydroxybenzoates as well as block polyether-esters derived from polyethers having hydroxyl end groups; also polyesters modified with polycarbonates or MBS.

18. Polycarbonates and polyester-carbonates.

19. Polysulfones, polyether-sulfones and polyetherketones.

20. Crosslinked polymers which are derived from aldehydes on the one hand and phenols, urea and melamine on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols, and vinyl compounds as crosslinking agents, and also halogen-containing modifications thereof of low inflammability.

23. Thermosetting acrylic resins, derived from substituted acrylic esters, crosslinkable for example epoxyacrylates, urethane-acrylates or polyester-acrylates.

24. Alkyd resins, polyester resins or acrylate resins crosslinked with melamine resins, urea resins, polyisocyanates or epoxide resins.

25. Crosslinked epoxide resins which are derived from polyepoxides, for example from bis-glycidyl ethers or from cycloaliphatic diepoxides.

26. Natural polymers, such as cellulose, natural rubber, gelatine and derivatives thereof which are chemically modified in a polymer-homologous manner, such as cellulose acetates, cellulose propionates and cellulose butyrates, or the cellulose ethers, such as methylcellulose; and rosins and their derivatives.

27. Mixtures (polyblends) of polymers as mentioned above, for example PP/EPDM, polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO.

The invention therefore also relates to compositions containing an organic material which is sensitive to oxidative, thermal or actinic degradation and at least one compound of the formula I, and to the use of compounds of the formula I for stabilizing organic material against oxidative, thermal or actinic degradation.

Preferred organic materials are polymers, for example synthetic polymers or thermoplastic polymers. Organic materials which are particularly preferred are polyolefins, for example polypropylene or polyethylene.

In general, the compounds of the formula I are added to the material to be stabilized in amounts of 0.01 to 10%, preferably 0.01 to 5% and particularly 0.01 to 2%, relative to the total weight of the material to be stabilized.

As well as the compounds of the formula I, the compositions according to the invention can contain, in addition, conventional additives, for example those indicated below.

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-di-cyclopentyl-4-methylphenol, 2-(α-methylcyclohexyl)-4,6-dimethylphenol, 2,6-di-octadecyl-4-methylphenol, 2,4,6-tricyclohexylphenol, 2,6-di-tert-butyl-4-methoxymethylphenol and 2,6-di-nonyl-4-methylphenol.

1.2. Alkylated hydroquinones, for example 2,6-di-tert-butyl-4-methoxyphenol, 2,5-di-tert-butylhydroquinone, 2,5-di-tert-amylhydroquinone and 2,6-diphenyl-4-octadecyloxyphenol.

1.3. Hydroxylated thiodiphenyl ethers, for example 2,2'-thiobis-(6-tert-butyl-4-methylphenol), 2,2'-thiobis-(4-octylphenol), 4,4'-thiobis-(6-tert-butyl-3-methylphenol) and 4,4'-thiobis-(6-tert-butyl-2-methylphenol).

1.4. Alkylidene bisphenols, for example 2,2'-methylenebis-(6-tert-butyl-4-methylphenol), 2,2'-methylenebis-(6-tert-butyl-4-ethylphenol), 2,2'-methylenebis-[4-methyl-6-(α-methylcyclohexyl)-phenol], 2,2'-methylenebis-(4-methyl-6-cyclohexylphenol), 2,2'-methylenebis-(6-nonyl-4-methylphenol), 2,2'-methylenebis-(4,6-di-tert-butylphenol), 2,2'-ethylidenebis-(4,6-di-tert-butylphenol), 2,2'-ethylidenebis-(6-tert-butyl-4-isobutylphenol), 2,2'methylenebis-[6-(α-methylbenzyl)-4-nonylphenol], 2,2'-methylenebis-[6-(α,α-dimethylbenzyl)-4-nonylphenol], 4,4'-methylenebis-(2,6-di-tert-butylphenol), 4,4'-methylenebis-(6-tert-butyl-2-methylphenol), 1,1-bis-(5-tert-butyl-4-hydroxy-2-methylphenyl)-butane, 2,6-bis-(3-tert-butyl-5-methyl-2-hydroxybenzyl)-4-methylphenol, 1,1,3-tris-(5-tert-butyl-4-hydroxy-2-methylphenyl)-butane, 1,1-bis-(5-tert-butyl-4-hydroxy-2-methylphenyl)-3-n-dodecylmercaptobutane, ethylene glycol bis-[3,3-bis-(3'-tert-butyl-4'-hydroxyphenyl)-butyrate], bis-(3-tert-butyl-4-hydroxy-5-methylphenyl)-dicyclopentadiene and bis-[2-(3'-tert-butyl-2'-hydroxy-5'-methylbenzyl)-6-tert-butyl-4-methylphenyl]terephthalate.

1.5. Benzyl compounds, for example, 1,3,5-tris-(3,5-di-tert-butyl-4-hydroxybenzyl)-2,4,6-trimethylbenzene, bis-(3,5-di-tert-butyl-4-hydroxybenzyl) sulfide, isooctyl 3,5-di-tert-butyl-4-hydroxybenzylmercaptoacetate, bis-(4-tert-butyl-3-hydroxy-2,6-dimethylbenzyl)-dithiolterephthalate, 1,3,5-tris-(3,5-di-tert-butyl-4-hydroxybenzyl) isocyanurate, 1,3,5-tris-(4-tert-butyl-3-hydroxy-2,6-dimethylbenzyl) isocyanurate, dioctadecyl 3,5-di-tert-butyl-4-hydroxybenzylphosphonate, the Ca salt of monoethyl 3,5-di-tert-butyl-4-hydroxybenzylphosphonate and 1,3,5-tris-(3,5-dicyclohexyl-4-hydroxybenzyl) isocyanurate.

1.6. Acylaminophenols, for example 4-hydroxylauranilide, 4-hydroxystearanilide, 2,4-bis-(octylmercapto)-6-(3,5-di-tert-butyl-4-hydroxyanilino)-s-triazine and octyl N-(3,5-di-tert-butyl-4-hydroxyphenyl)carbamate.

1.7. Esters of β-(3,5-di-tert-butyl-4-hydroxyphenyl)-propionic acid, with monohydric or polyhydric alcohols, for example with methanol, octadecanol, 1,6-hexanediol, neopentyl glycol, thiodiethylene glycol, diethylene glycol, triethylene glycol, pentaerythritol, tris-(hydroxyethyl) isocyanurate and N,N'-bis-(hydroxy)ethyloxamide.

1.8. Esters of β-(5-tert-butyl-4-hydroxy-3-methylphenyl)-propionic acid with monohydric or polyhydric alcohols, for example with methanol, octadecanol, 1,6-hexanediol, neopentyl glycol, thiodiethylene glycol, diethylene glycol, triethylene glycol, pentaerythritol, tris-(hydroxy)ethyl isocyanurate and N,N'-bis-(hydroxyethyl)oxamide.

1.9. Esters of β-(3,5-dicyclohexyl-4-hydroxyphenyl)-propionic acid with monohydric or polyhydric alcohols, for example with methanol, octadecanol, 1,6-hexanediol, neopentyl glycol, thiodiethylene glycol, diethylene glycol, triethylene glycol, pentaerythritol, tris-(hydroxy)ethyl isocyanurate and N,N'-bis-(hydroxyethyl)oxamide.

1.10. Amides of β-(3,5-di-tert-butyl-4-hydroxyphenyl)-propionic acid, for example N,N'-bis-(3,5-di-tert-butyl-4-hydroxyphenylpropionyl)-hexamethylenediamine, N,N'-bis-(3,5-di-tert-butyl-4-hydroxyphenylpropionyl)-trimethylenediamine and N,N'-bis-(3,5-di-tert-butyl-4-hydroxyphenylpropionyl)-hydrazine.

2. UV absorbers and light stabilizers 2.1. 2-(2'-Hydroxyphenyl)-benzotriazoles, for example the 5'-methyl-, 3',5'-di-tert-butyl-, 5'-tert-butyl, 5'-(1,1,3,3-tetramethylbutyl), 5-chloro-3',5'-di-tert-butyl, 5-chloro-3'-tert-butyl-5'-methyl, 3'-sec-butyl-5'-tert-butyl, 4'-octoxy, 3',5'-di-tert-amyl and/or 3',5'-bis-(α,α-dimethylbenzyl) derivatives.

2.2. 2-Hydroxybenzophenones, for example the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivatives.

2.3. Esters of substituted or unsubstituted benzoic acids, for example 4-tert-butylphenyl salicylate, phenyl salicylate, octylphenyl salicylate, dibenzoylresorcinol, bis-(4-tert-butylbenzoyl)-resorcinol, benzoylresorcinol, 2,4-di-tert-butylphenyl 3,5-di-tert-butyl-4-hydroxybenzoate and hexadecyl 3,5-di-tert-butyl-4-hydroxybenzoate.

2.4. Acrylates, for example ethyl or isooctyl α-cyano-β,β-diphenylacrylate, methyl α-carbomethoxycinnamate, methyl or butyl α-cyano-β-methyl-p-methoxycinnamate, methyl α-carbomethoxy-p-methoxycinnamate and N-(β-carbomethoxy-β-cyanovinyl)-2-methylindoline.

2.5 Nickel compounds, for example nickel complexes of 2,2'-thiobis-[4-(1,1,3,3-tetramethylbutyl)-phenol], such as the 1:1 complex or the 1:2 complex, if appropriate with additional ligands, such as n-butylamine, triethanolamine or N-cyclohexyldiethanolamine, nickel dibutyldithiocarbamate, nickel salts of monoalkyl 4-hydroxy-3,5-di-tert-butylbenzylphosphonates, such as the methyl or ethyl ester, nickel complexes of ketoximes, such as of 2-hydroxy-4-methylphenyl undecyl ketoxime, and nickel complexes of 1-phenyl-4-lauroyl-5-hydroxypyrazole, if appropriate with additional ligands.

2.6. Sterically hindered amines, for example bis-(2,2,6,6-tetramethylpiperidyl) sebacate, bis-(1,2,2,6,6-pentamethylpiperidyl) sebacate, bis-(1,2,2,6,6-pentamethylpiperidyl) n-butyl-3,5-di-tert-butyl-4-hydroxybenzylmalonate, the condensation product formed from 1-hydroxyethyl-2,2,6,6-tetramethyl-4-hydroxypiperidine and succinic acid, the condensation product formed from N,N'-bis-(2,2,6,6-tetramethyl-4-piperidyl)-hexamethylenediamine and 4-tert-octylamino-2,6-dichloro-1,3,5-s-triazine, tris-(2,2,6,6-tetramethyl-4-piperidyl) nitrilotriacetate, tetrakis-(2,2,6,6-tetramethyl-4-piperidyl) 1,2,3,4-butanetetraoate and 1,1'-(1,2-ethanediyl)-bis-(3,3,5,5-tetramethylpiperazinone).

2.7. Oxamides, for example 4,4'-di-octyloxyoxanilide, 2,2'-di-octyloxy-5,5'-di-tert-butyloxanilide, 2,2'-didodecyloxy-5,5'-di-tert-butyloxanilide, 2-ethoxy-2'-ethyloxanilide, N,N'-bis-(3-dimethylaminopropyl)-oxamide, 2-ethoxy-5-tert-butyl-2'-ethyloxanilide and a mixture thereof with 2-ethoxy-2'-ethyl-5,4'-di-tert-butyloxanilide, and mixtures of o-methoxy- and p-methoxy-disubstituted oxanilides and of o-ethoxy- and p-ethoxy-disubstituted oxanilides.

2.8. 2-(2-Hydroxyphenyl)-1,3,5-triazines, for example 2,4,6-tris-(2-hydroxy-4-octyloxyphenyl)-1,3,5-triazine, 2-(2-hydroxy-4-octyloxyphenyl)-4,6-bis-(2,4-dimethylphenyl)-1,3,5-triazine, 2-(2,4-dihydroxyphenyl)-4,6-bis-(2,4-dimethylphenyl)-1,3,5-triazine, 2,4-bis-(2-hydroxy-4-propyloxyphenyl)-6-(2,4-dimethylphenyl)-1,3,5-triazine, 2-(2-hydroxy-4-octyloxyphenyl)-4,6-bis-(4-methylphenyl)-1,3,5-triazine and 2-(2-hydroxy-4-dodecyloxyphenyl)-4,6-bis-(2,4-dimethylphenyl)-1,3,5-triazine.

3. Metal deactivators, for example N,N'-diphenyloxamide, N-salicylal-N'-salicyloylhydrazine, N,N'-bis-(salicyloyl)-hydrazine, N,N'-bis-(3,5-di-tert-butyl-4-hydroxyphenylpropionyl)-hydrazine, 3-salicyloylamino-1,2,4-triazole and bis-(benzylidene)-oxalic acid dihydrazide.

4. Phosphites and phosphonites, for example triphenyl phosphite, diphenyl alkyl phosphites, phenyl dialkyl phosphites, tris-(nonylphenyl) phosphite, trilauryl phosphite, trioctadecyl phosphite, distearyl pentaerythrityl diphosphite, tris-(2,4-di-tert-butylphenyl) phosphite, diisodecyl pentaerythrityl diphosphite, bis-(2,4-di-tert-butylphenyl) pentaerythrityl diphosphite, tristearyl sorbitol triphosphite, tetrakis-(2,4-di-tert-butylphenyl) 4,4'-biphenylenediphosphonite and 3,9-bis-(2,4-di-tert-butylphenoxy)-2,4,8,10-tetraoxa-3,9-diphosphaspiro[5.5]undecane.

5. Compounds which destroy peroxides, for example esters of β-thiodipropionic acid, for example the lauryl, stearyl, myristyl or tridecyl ester, mercaptobenzimidazole, the zinc salt of 2-mercaptobenzimidazole, zinc dibutyldithiocarbamate, dioctadecyl disulfide and pentaerythrityl tetrakis-(β-dodecylmercapto)-propionate.

6. Polyamide stabilizers, for example copper salts in combination with iodides and/or phosphorus compounds and salts of divalent manganese.

7. Basic co-stabilizers, for example melamine, polyvinylpyrrolidone, dicyandiamide, triallyl cyanurate, urea derivatives, hydrazine derivatives, amines, polyamides, polyurethanes, alkali and alkaline earth metal salts of higher fatty acids, for example Ca stearate, Zn stearate, Mg stearate, Na ricinoleate and K palmitate, antimony pyrocatecholate or tin pyrocatecholate.

8. Nucleating agents, for example 4-tert-butylbenzoic acid, adipic acid or diphenylacetic acid.

9. Fillers and reinforcing agents, for example calcium carbonate, silicates, glass fibres, asbestos, talc, kaolin, mica, barium sulfate, metal oxides and hydroxides, carbon black and graphite.

10. Other additives, for example plasticizers, lubricants, emulsifiers, pigments, fluorescent whiteners, fire-retarding agents, antistatic agents and blowing agents.

The conventional additives are added, for example, in concentrations of 0.01 to 10%, relative to the total weight of the material to be stabilized.

The incorporation of the compounds of the formula I and, if desired, other additives into the polymeric, organic material is effected by known methods, for example before or during shaping or by applying the compounds in dissolved or dispersed form to the polymeric, organic material, if appropriate with subsequent evaporation of the solvent. The compounds of the formula I can also be added to the materials to be stabilized in the form of a master batch in which they are present in a concentration of, for example, 2.5 to 25% by weight.

The compounds of the formula I can also be added before or during polymerization or before crosslinking.

The compounds of the formula I can be incorporated into the material to be stabilized in an undiluted form or encapsulated in waxes, oils or polymers.

The compounds of the formula I can also be sprayed onto the polymer to be stabilized. They are capable of diluting other additives (for example the conventional additives indicated above) or melts thereof in such a way that they can also be sprayed onto the polymer to be stabilized together with these additives. Addition by spraying on during the deactivation of the polymerization catalysts is particularly advantageous, it being possible, for example, to use for spraying the steam used for deactivation.

In the case of polyolefins polymerized in spherical form it can be advantageous, for example, to apply the compounds of the formula I by spraying on, if appropriate together with other additives.

A preferred embodiment of the present invention is, therefore, the use of compounds of the formula I for stabilizing polymers against oxidative, thermal or actinic degradation, the compounds of the formula I being sprayed onto the polymer.

The materials thus stabilized can be used in a very wide variety of shapes, for example as films, fibres, tapes, moulding materials or profiles or as binders for paints, adhesives or putties.

The compounds of the formula I can be prepared analogously to known processes; for example by condensation of phenols of the formula II

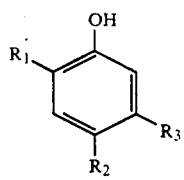

(II)

in which $R_1$, $R_2$ and $R_3$ are as defined above with 1–1.3 mol of mandelic acid or a mandelic acid derivative, as described in GB-A 2,042,562. Instead of mandelic acid or a mandelic acid derivative, it is also possible to use a compound of the formula III or IV

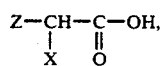

(III)

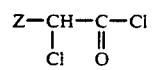

(IV)

in which Z is as defined above and X is, for example, acetoxy, tolylsulfonyloxy or mesitylsulfonyloxy. If a compound of the formula IV is used, it is appropriate to use the process described in Example 3 of BE-A 881,496.

The reactions are preferably carried out within a temperature range from 180° to 220° C. and under a pressure of 10–1013 mbar.

Insofar as they are not commercially available, the compounds of the formula II can be prepared analogously to known processes; for example by catalytic alkylation of phenols of the formula

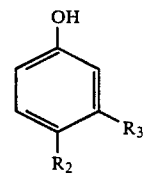

with linear α-olefins ($C_{13}$–$C_{30}$). Alkylation is mainly carried out in the liquid phase without using a solvent.

The following may be mentioned as suitable catalysts:
a) Friedel-Crafts catalysts, for example proton acids (sulfuric acid, phosphoric acid, p-toluenesulfonic acid etc), solid inorganic catalysts (acid-activating bleaching earths, for example montmorillonite types, oxides of aluminium and silicon etc) and other Friedel-Crafts catalysts (boron trifluoride, aluminium chloride, ferric(III)chloride, zinc chloride etc),
b) o-selective catalysts, for example aluminium phenates and γ-aluminium oxide, as described in U.S. Pat. No. 3,367,981 and DE-B 1,142,873, and also other modifications of aluminium oxide.

o-Selective catalysts are preferred, and the active γ-aluminium oxide described in the abovementioned US-A and DE-B is particularly preferred.

In the presence of Friedel-Crafts catalysts, the reaction is appropriately carried out under "normal pressure" within the temperature range from, for example, 30° to 150° C. In the case of alkylation in the presence of o-selective catalysts, it is advantageous to carry out the reaction at an elevated temperature (approx. 200°–350° C.) under pressure (approx. 20–200 bar).

After the alkylation the catalyst is removed from the crude material, for example by extraction by washing or filtration, and the latter can then be purified by distillation.

The compounds of the formula II can be obtained in the form of a mixture of isomers which can be separated, for example, by means of chromatographic methods, in particular gas chromatography and high-pressure liquid chromatography (HPLC). It is also possible, however, to employ the mixture of isomers for the preparation of the compounds of the formula I, so that the compounds of the formula I are also obtained as a mixture of isomers. This mixture of isomers of the compounds of the formula I can, if necessary, be separated or can be used without treatment for stabilizing organic materials against oxidative, thermal or actinic degradation.

It is also possible to employ commercially available mixtures of olefins ($H_2C=CH-CH_2-A_1$ in which $A_1$ is, for example, $C_{13}$–$C_{17}$alkyl, $C_{17}$–$C_{21}$alkyl or $C_{21}$–$C_{27}$alkyl) for the preparation of the compounds of the formula II.

The following examples illustrate the invention further. Unless stated otherwise, parts and percentages are by weight.

EXAMPLE 1

Preparation of the compound 3-phenyl-7-(1'-hexadecylethyl)-benzofuran-2-one 4.8 g (31.5 mmol) of mandelic acid and 10.4 g (30 mmol) of 1-hexadecylethylphenol are heated together at 190°–200° C. for approx. 8 hours under reduced pressure (13.3 mbar). In the course of this the water formed in the reaction is removed by distillation. When the reaction is complete, the reaction product is filtered over silica gel (hexane) and is then treated with cold hexane. The product has a melting point of 60°–62° C. and is in the form of a white powder. The yield is 7 g (=50% of theory).

| Elementary analysis: | | |
|---|---|---|
| Calculated: | C 83.06%; | H 10.02% |
| Found: | C 83.04%; | H 10.02% |

EXAMPLES 2-5

The compounds indicated in Table 1 are prepared analogously to Example 1.

TABLE 1

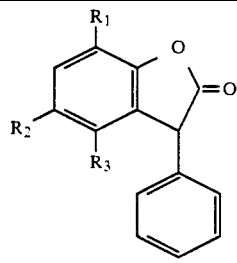

| Example | $R_1$ | $R_2$ | $R_3$ | M.p. | Elementary analysis |
|---|---|---|---|---|---|
| 2 | 1-Hexadecylethyl | —H | —CH$_3$ | Oil | calcd.: C 83.14%; H 10.15%<br>found: C 83.11%; H 10.33% |
| 3 | 1-Hexadecylethyl | —CH$_3$ | —H | 42° C. | calcd.: C 83.14%; H 10.15%<br>found: C 83.43%; H 10.33% |
| 4 | 1-Dodecylethyl | —CH$_3$ | —H | Oil | calcd.: C 82.81%; H 9.59%<br>found: C 82.88%; H 9.76% |
| 5 | 1-Hexadecylethyl | —C(CH$_3$)$_3$ | —H | Oil | calcd.: C 83.34%; H 10.49%<br>found: C 83.47%; H 10.47% |

EXAMPLE 6

Stabilization of polypropylene.

1.3 kg of polypropylene powder (melt index: 3.2 g/10 minutes, measured at 230° C./2.16 kg) are mixed with 0.05% of calcium stearate, 0.05% of tetrakis-[3,5-di-tert-butyl-4-hydroxyphenylpropionyloxymethyl]-methane and 0.05% of the stabilizer shown in Table 2. This mixture is extruded at 100 revolutions per minute in an extruder having a cylinder diameter of 20 mm and a length of 400 mm, the 3 heating zones being adjusted to 260° C., 270° C. and 280° C. The extrudate is drawn through a water bath to cool it and is then granulated. The resulting granules are extruded for a second and third time. After these 3 extrusions, the melt index is measured at 230° C./2.16 kg. The results are shown in Table 2.

TABLE 2

| Compound from Example No. | Melt index*) [g/10 min] at 230° C./2.16 kg |
|---|---|
| — | 17.2 |
| 1 | 4.6 |
| 2 | 5.9 |
| 3 | 4.5 |
| 4 | 4.3 |

*)Low values mean good stabilization.

What is claimed is:

1. A compound of the formula I

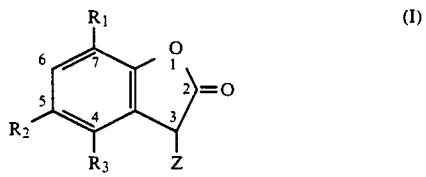

in which $R_1$ is $C_{14}$–$C_{18}$alkyl, $R_2$ is hydrogen, $C_1$–$C_4$alkyl, $C_5$–$C_{12}$cycloalkyl, $C_5$–$C_7$cycloalkyl which is substituted by $C_1$–$C_4$alkyl, or is phenyl or $C_7$–$C_{12}$phenylalkyl, $R_3$ is hydrogen or $C_1$–$C_4$alkyl and Z is phenyl, phenyl which is substituted by $C_1$–$C_8$alkyl, $C_1$–$C_4$alkoxy or chlorine, a group

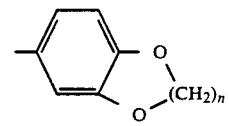

in which n is 1 or 2 or a group

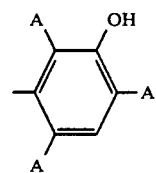

in which the radicals A independently of one another are $C_1$–$C_8$alkyl, methoxy or ethoxy.

2. A compound according to claim 1, wherein Z is phenyl.

3. A compound according to claim 1, wherein $R_2$ is hydrogen, $C_1$–$C_4$alkyl, cyclohexyl, phenyl or benzyl.

4. A compound according to claim 1, wherein $R_2$ is hydrogen or $C_1$–$C_4$alkyl.

5. A compound according to claim 1, wherein $R_3$ is hydrogen or methyl.

6. A compound according to claim 1, wherein $R_2$ and $R_3$ independently of one another are hydrogen or $C_1$–$C_4$alkyl.

7. The compounds 3-phenyl-7-(1'-hexadecylethyl)benzofuran-2-one, 3-phenyl-5-methyl-7-(1'-hexadecylethyl)benzofuran-2-one, 3-phenyl-5-methyl-7-(1'-dodecylethyl)benzofuran-2-one, 3-phenyl-5-tert-butyl-7-(1'-hexadecylethyl)benzofuran-2-one or 3-phenyl-4-methyl-7-(1'-hexadecylethyl)benzofuran-2-one according to claim 1.

8. The compound 3-phenyl-5-methyl-7-(1'-dodecylethyl)benzofuran-2-one according to claim 1.

* * * * *